(12) United States Patent
Forster

(10) Patent No.: US 10,416,073 B2
(45) Date of Patent: Sep. 17, 2019

(54) RADIO FREQUENCY IDENTIFICATION SENSOR ASSEMBLY

(71) Applicant: Avery Dennison Corporation, Pasadena, CA (US)

(72) Inventor: Ian J. Forster, Essex (GB)

(73) Assignee: AVERY DENNISON RETAIL INFORMATION SERVICES, LLC, Mentor, OH (US)

( * ) Notice: Subject to any disclaimer, the term of this patent is extended or adjusted under 35 U.S.C. 154(b) by 151 days.

(21) Appl. No.: 13/838,503

(22) Filed: Mar. 15, 2013

(65) Prior Publication Data

US 2013/0284905 A1  Oct. 31, 2013

Related U.S. Application Data

(60) Provisional application No. 61/640,030, filed on Apr. 30, 2012.

(51) Int. Cl.
  *H01L 31/00* (2006.01)
  *G01N 21/25* (2006.01)
  (Continued)

(52) U.S. Cl.
  CPC ....... *G01N 21/255* (2013.01); *G06K 19/0717* (2013.01); *G06K 19/0723* (2013.01); *G06K 19/0728* (2013.01); *G06K 19/07749* (2013.01)

(58) Field of Classification Search
  CPC ........... G06K 19/0717; G06K 19/0723; G06K 19/0728; G06K 19/07749; G01N 21/25; G01N 21/31; G01N 21/255
  (Continued)

(56) References Cited

U.S. PATENT DOCUMENTS 5,239,406 A * 8/1993 Lynam .................... B32B 17/10
   296/215
6,193,912 B1 * 2/2001 Thieste .................... C09K 9/02
   252/583

(Continued)

FOREIGN PATENT DOCUMENTS

WO   WO-2008148220   12/2008

OTHER PUBLICATIONS

Cho, N., et al., "A 5.1-μW UHF RFID Tag Chip Integrated with Sensors for Wireless Environmental Monitoring", Proceedings of the Solid-State Circuits European Conference—ESSCIRC, 2005 (Sep. 12, 2005), [retrieved on Sep. 24, 2013] Retrieved from the Internet: <URL: http://ssl.kaist.ac.kr/2007/data/conference/NJCHO_ESSCIRC2005.pdf>, 4 pgs.

(Continued)

*Primary Examiner* — Georgia Y Epps
*Assistant Examiner* — Kevin Wyatt
(74) *Attorney, Agent, or Firm* — Avery Dennison Retail Information Services, LLC

(57) ABSTRACT

An RFID sensor comprises an RFID chip, an antenna, and sensing material. The RFID chip is in electrical communication with the antenna and comprises an optical sensor. The sensing material overlies an upper surface of the RFID chip and is configured as a variable light filter that filters light differently depending upon certain properties or conditions of the environment surrounding the RFID sensor. A light source is configured to selectively illuminate the sensing material to facilitate detection of certain properties or conditions of the environment surrounding the RFID sensor.

20 Claims, 7 Drawing Sheets

(51) Int. Cl.
 *G06K 19/07* (2006.01)
 *G06K 19/077* (2006.01)
(58) Field of Classification Search
 USPC .................. 250/214.1, 484.5; 235/379, 492;
 340/572.1; 435/287.2; 705/15
 See application file for complete search history.

(56) References Cited

U.S. PATENT DOCUMENTS

| | | | |
|---|---|---|---|
| 7,009,496 | B2 | 3/2006 | Arneson |
| 7,819,328 | B2* | 10/2010 | Levinson ............. G06K 7/0008 |
| | | | 235/492 |
| 7,844,505 | B1 | 11/2010 | Arneson |
| 8,742,900 | B2* | 6/2014 | Burr .................. H05B 37/0272 |
| | | | 340/10.33 |
| 2007/0096882 | A1 | 5/2007 | Bandy |
| 2007/0298487 | A1* | 12/2007 | Bachur et al. ............. 435/287.2 |
| 2008/0246613 | A1 | 10/2008 | Linstrom |
| 2009/0179751 | A1* | 7/2009 | Forster .......................... 340/501 |
| 2009/0237223 | A1 | 9/2009 | Zimmerman |
| 2010/0079416 | A1* | 4/2010 | Chung ................ G02F 1/13336 |
| | | | 345/204 |
| 2010/0156640 | A1* | 6/2010 | Forster ....................... 340/572.1 |
| 2011/0036913 | A1* | 2/2011 | Merz et al. .................... 235/492 |
| 2012/0031979 | A1* | 2/2012 | Kang ................. G06K 19/0717 |
| | | | 235/492 |

OTHER PUBLICATIONS

Swelberg, C., "Howard Memorial Finds RFID Keeps Assets From Getting Lost" [online]. RFID Journal LLC, Sep. 23, 2009 [retrieved on Sep. 24, 2013]. Retrieved from the Internet: <URL: http://www.rfidjournal.com/articles/view?5244>, 2 pgs.

International Preliminary Report on Patentability and Written Opinion dated Nov. 4, 2014 for International Application No. PCT/US2013/32310.

International Search Report dated Jul. 1, 2013 for International Application No. PCT/US2013/32310.

* cited by examiner

RADIO FREQUENCY IDENTIFICATION SENSOR ASSEMBLY

CROSS-REFERENCE TO RELATED APPLICATION

The present application claims the benefit of U.S. Provisional Patent Application No. 61/640,030 filed Apr. 30, 2012, which is incorporated herein by reference in its entirety.

BACKGROUND

A conventional radio frequency identification (RFID) tag can be deployed to sense environmental conditions and communicate environmental data to a nearby RFID reader.

SUMMARY

In accordance with one embodiment, an RFID sensor comprises an RFID chip, an antenna, and sensing material. The RFID chip is in electrical communication with the antenna and is arranged to function as an optical sensor. The sensing material overlies an upper surface of the RFID chip and is configured as a variable light filter that filters light differently depending upon certain properties or conditions of the environment surrounding the RFID sensor. A light source is configured to selectively illuminate the sensing material to facilitate detection of certain properties or conditions of the environment surrounding the RFID sensor.

In accordance with another embodiment, a method for detecting properties or conditions of an environment comprises overlaying a sensing material onto an RFID chip of an RFID sensor. The RFID chip is configured to function as an optical sensor and the sensing material is configured as a variable light filter that filters light differently depending upon the properties or conditions of the environment surrounding the RFID sensor. The method further comprises directing light from a light source towards the RFID sensor and detecting the response of the RFID sensor.

In accordance with another embodiment, a method for detecting properties or conditions of an environment comprises overlaying a sensing material onto a first RFID chip, whereupon a second RFID chip, that is part of the same structure or is co-located, has either an inert material, or the same sensing material isolated from the environment, where the measurement is in the form of looking at the difference between the first and second chip in response to a light source.

In accordance with another embodiment, the light source for the sensing function is the ambient illumination where the sensor is located. In a further variation the structure includes a method on concentrating the incident optical illumination, such as a lense or mirror, including a Fresnel lense.

BRIEF DESCRIPTION OF THE DRAWINGS

It is believed that certain embodiments will be better understood from the following description taken in conjunction with the accompanying drawings in which.

DETAILED DESCRIPTION

The apparatus and methods disclosed in this document are described in detail by way of examples and with reference to FIGS. 1-7. Unless otherwise specified, like numbers in FIGS. 1-7 indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be, and should not be, construed as mandatory or limiting unless specifically designated as such. Selected examples of apparatus and methods for a radio frequency identification sensor assembly are hereinafter disclosed and described in detail with reference made to FIGS. 1-7.

Figure 1:
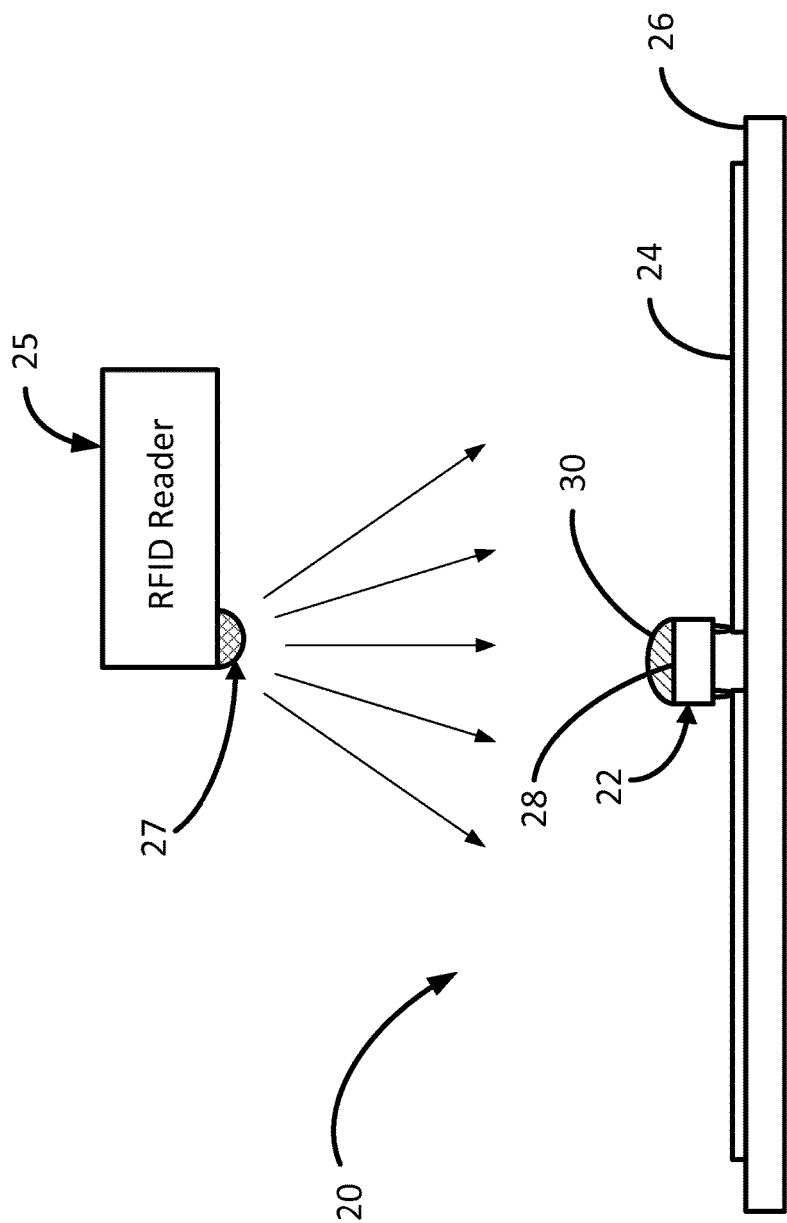
FIG. 1 is a schematic view depicting an RFID sensor and an RFID reader in accordance with one embodiment, the RFID reader having a light source.

As illustrated in FIG. 1, an RFID sensor 20 can include an RFID chip 22 and an antenna 24. The RFID chip 22 can be arranged to store and/or derive information and encode such information onto a radio signal generated by or passing through the RFID chip 22. The antenna 24 can be electrically coupled with the RFID chip 22. The antenna 24 can be arranged to facilitate communication between the RFID sensor assembly 20 and remote devices such as, for example, an RFID reader 25 or RFID transceiver. For example, the antenna 24 can receive signals from remote devices (e.g., an interrogation signal) and can direct those signals to the RFID chip 22. The antenna 24 can also receive signals from the RFID chip 22 (e.g., reply signals) and can send or transmit such signals to be received and read by remote devices.

The RFID chip 22 and the antenna 24 can be supported by a substrate 26. The substrate 26 can comprise a rigid or flexible material such as paper, plastic sheeting, or the like. The substrate 26 can also be a single material or a composite of a number of materials arranged to facilitate the operation of the RFID sensor 20. The RFID chip 22 and the antenna 24 can be adhered to the substrate 26 (e.g., with adhesive), deposited directly onto the substrate 26 (e.g., through a printing process), or provided on the substrate 26 in any of a variety of other suitable alternative arrangements.

As will be understood, the RFID sensor 20 can be configured to detect certain properties or conditions of the environment surrounding the RFID sensor 20 (e.g., sensed condition or parameters) such as changes in humidity, temperature, atmospheric pressure, pH (e.g., for a liquid), or any other environmental conditions surrounding the RFID sensor 20 and/or the presence and/or magnitude of a specific or general class of airborne chemical agents or chemicals (e.g., carbon monoxide and/or radon). As illustrated in FIG. 1, the RFID reader 25 can include a light source 27 that is configured to selectively direct or otherwise provide light to a nearby RFID sensor 20.

The RFID chip 22 can be arranged so that the behavior of the RFID chip 22 or the behavior of a portion of the RFID chip 20 is affected by its interaction with light or other optical energy. When light is directed to the RFID sensor 20, the light can affect the behavior of the RFID chip 22, and the effect on the RFID chip's 22 behavior can be encoded onto a reply signal generated by the RFID sensor 20. The reply signal from the RFID sensor 20 can be received and interpreted by the RFID reader 25 to determine the significance of the behavior of the RFID chip 22. This is to say that the RFID chip 22 can be configured as an optical sensor that can be used to determine environmental conditions or parameters based on its interaction with light.

Referring again to FIG. 1, the RFID chip 22 can include an upper surface 28 that can be exposed to light. A sensing material 30 can be positioned proximate to the upper surface 28 so that the sensing material 30 is positioned between a source of light such as the light source 27 attached to the RFID reader 25 and the upper surface 28 of the RFID chip 22. The sensing material 30 can be configured so that the properties of the sensing material 30 properties altered, modified or otherwise changed by environmental conditions encountered by the RFID sensor 20. Such changes to the properties of the sensing material 30 can cause the sensing material 30 to act as a variable light filter that filters light differently depending on the environmental condition surrounding the RFID sensor 20. When light is directed to or otherwise provided to the RFID sensor 20 (e.g., from the light source 27), the amount of light permitted through to the sensing material 30 and onto the upper surface 28 can be a function of the presence and/or concentration of the sensed condition or parameter. The sensed condition or parameter can accordingly be detected through the change in behavior of the RFID chip due to the light that reaches the RFID chip 22.

As will be understood, the sensing material 30 can be arranged so that environmental conditions or parameters surrounding or contacting the RFID sensor 20 can alter, modify, or otherwise change the sensing material 30 in any number of ways. For example, in one embodiment, the opacity of the sensing material 30 can change in proportion to the presence and/or concentration of the sensed condition or parameter surrounding the RFID sensor 20. The higher the concentration of the sensed condition or parameter, the more opaque the sensing material 30 becomes. Therefore, the less light is allowed to pass through the sensing material 30 to engage the surface 28 of the RFID chip 22. Because the behavior of the RFID chip 22 can be affected by the amount of light that interacts with the RFID chip 22, the concentration of the sensed condition or parameter can be proportional to the change in behavior of the RFID chip 22. Therefore, the change in behavior of the RFID chip 22 due to interaction with the light can be used to determine the concentration of the environmental condition or parameter surrounding or contacting the RFID sensor 20.

Although the example above describes a change in the opacity of sensing material 30 due to the presence of an environmental condition or parameter, it will be understood that other properties of the sensing material 30 can change based on the presence of an environmental condition or parameter. For example, the sensing material can become more or less reflective or absorb more or less light in response to changes to an environmental condition or parameter.

In one embodiment, the sensing material 30 can comprise a thermochromic material that changes color in response to heat. In another embodiment, the sensing material 30 can be a biomimetic sensor that darkens in the presence of carbon monoxide. In another embodiment, the sensing material 30 can be a titanium oxide compound or a palladium oxide compound that changes color in the presence of hydrogen gas. In other embodiments, any of a variety of suitable alternative optical properties of the sensing material 30 such as its opacity, reflectivity, absorption, and refractivity, for example, can vary in response to changes in the sensed environmental conditions or parameter. It will be appreciated that changes to the color, opacity, reflectivity, absorption, and refractivity, or other optical property can filter, absorb, redirect or otherwise deflect light that would otherwise reach the upper surface 28 of the RFID chip 22.

It will be appreciated that the detecting capabilities of the RFID sensor 20 can be selected based upon a particular application. For example, the RFID sensor 20 can be configured to detect relative humidity and can be attached to a shipping container to monitor for levels of relative humidity that could be harmful to the contents of the shipping container. In another example, the RFID sensor 20 can be configured to detect bio-hazardous materials and can be provided as part of a public transportation system to monitor for levels of bio-hazardous materials that could affect the well-being of its passengers. In another example, the RFID sensor 20 can be configured to detect air quality and can be provided as part of an environmental study to determine the overall air quality of a particular geographical location. Similarly, the RFID sensor 20 can be arranged to detect airborne chemicals or liquid chemicals that come into contact with the sensing material 30.

The sensing material 30 can be adhered to the upper surface 28 (e.g., with adhesive), deposited directly onto the upper surface 28 (e.g., through a printing process such as ink jet printing), or provided on the upper surface 28 in any of a variety of other suitable alternative arrangements. In one embodiment, a general purpose (e.g., conventional, off-the shelf type) RFID chip can be utilized as the RFID chip 22 for the RFID sensor 20. Typically, these general purpose RFID chips are inherently sensitive to near-infrared light. For example, when near-infrared light is projected onto a general purpose RFID chip, the near-infrared light can cause a reduction in the power sensitivity of the reply signal. In one example, the more infrared light at the upper surface of the general purpose RFID chip, the more the power sensitivity of the reply signal is depleted. The sensing material 30 can be applied over the general purpose RFID chip (e.g., over its upper surface as part of a post-production process) to effectively convert the general purpose RFID chip into an optical sensor for use in the RFID sensor 20.

In such an arrangement, the sensing material 30 can be configured as a variable near-infrared light filter that changes its color, opacity or other near-infrared filtering property, in response to the sensed condition or parameter. The light source 27 can be configured to transmit near-infrared light. When near-infrared light is provided onto the sensing material 30 from the light source 27, the sensed condition or parameter can be detected from the power sensitivity of the reply signal of the RFID chip 22. Exploiting the inherent behavior of these conventional RFID chips to the infrared light can be more cost effective and efficient than designing or tailoring an optical sensor which can oftentimes require specialized manufacturing techniques.

It will be appreciated that subjecting a general purpose RFID chip to infrared light can cause any of a variety of other behaviors and that the RFID reader 25 can be configured to detect those behaviors to facilitate detection of the sensed condition or parameter. It will also be appreciated that the RFID chip 22, light source 27, and/or sensing material 30 can be configured to be sensitive to any spectral range, such as an ultra-violet light spectrum or a microwave spectrum, for example.

In one embodiment, the light source 27 can be selectively operated by the RFID reader 25 based upon the communication status between the RFID reader 25 and the RFID sensor 20. When the RFID reader 25 and the RFID sensor 20 are not in communication with each other (e.g., when the RFID reader 25 is out of range), the light source 27 can be deactivated. When the RFID reader 25 and the RFID sensor 20 establish communication with each other, the light source 27 can be activated to facilitate detection of the sensed condition or parameter from the reply signal of the RFID sensor 20. The RFID reader 25 can be arranged to periodically activate the light source 27 to monitor the change in a condition or parameter over time. In another embodiment, the RFID reader 25 can control operation of the light source 27 once the RFID sensor 20 according to the relative distance between the light source 27 and the RFID reader 25. In another embodiment, the light source 27 can remain on during operation of the RFID reader 25.

When the RFID reader 25 and the RFID chip 22 initially communicate with each other, the light source 27 can remain off such that the sensing function of the RFID sensor 20 is not activated. The response of the RFID sensor 20 with the light source 27 off can serve as a real-time reference value for the RFID reader 25. The RFID reader 25 can then turn on the light source 27 to illuminate the RFID sensor 20 and the response of the RFID sensor 20 can be compared to the reference value to facilitate determination of detection of the sensed condition or parameter. In another embodiment, a reference value can be stored upon a memory device (e.g., non-volatile memory) of the RFID reader 25. When the RFID sensor 20 and the RFID reader 25 establish communication with each other, the reply signal from the RFID chip 22 can be compared to the stored reference value which can be more efficient that establishing a real-time reference value as indicated above. It will be appreciated that the RFID reader 25 can be provided with a predefined reference value for a plurality of different types of RFID sensors 20. When the RFID reader 25 established communication with the RFID sensor 20, the type of RFID sensor can be determined from the reply signal (e.g., through unique addressing) and the appropriate predetermined reference value can be recalled from memory and compared with the reply signal from the RFID chip 22.

Figure 2:
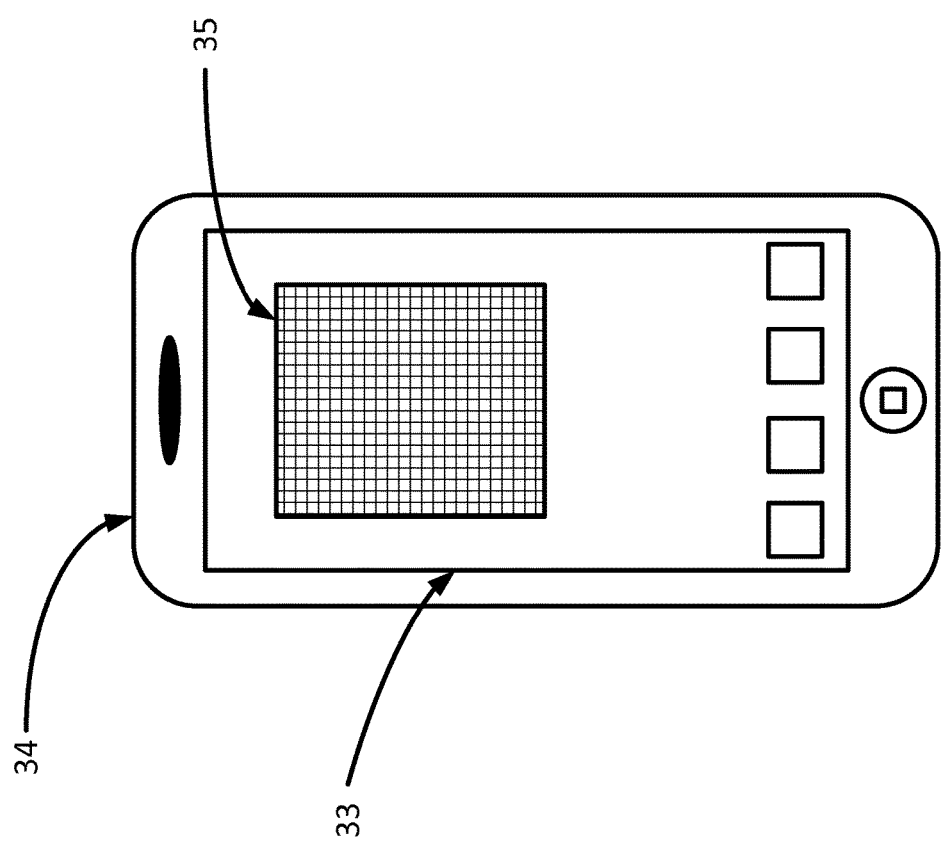
FIG. 2 is a top plan view depicting a smartphone having a screen displaying a color patch as a light source.

Although the light source 27 is described as being incorporated into the RFID reader 25, it will be appreciated that any of a variety of suitable alternative light source arrangements can be provided. For example, the light source 27 can be a stand-alone light source that is operated manually (e.g., through use of a manual pushbutton). In such an arrangement, the RFID reader 25 can be manually controlled and/or can provide cues to a user to coordinate operation of the light source 27 with the RFID reader 25. In another example, as illustrated in FIG. 2, a screen 33 of a smartphone 34 can be provided as a light source. The smartphone 34 can be configured as a near field communication (NFC) device. When a user encounters one of the RFID sensors 20, the screen 34 of the smartphone can be activated with a multi-color patch 35. The multi-colored patch 35 can be directed toward to the RFID sensor 20 to impart multi-colored light onto the RFID chip 22. The response of the RFID sensor 20 can be detected by an NFC reader (not shown) provided on the smartphone to facilitate detection of the presence and/or concentration of the sensed condition or parameter.

Figure 3:
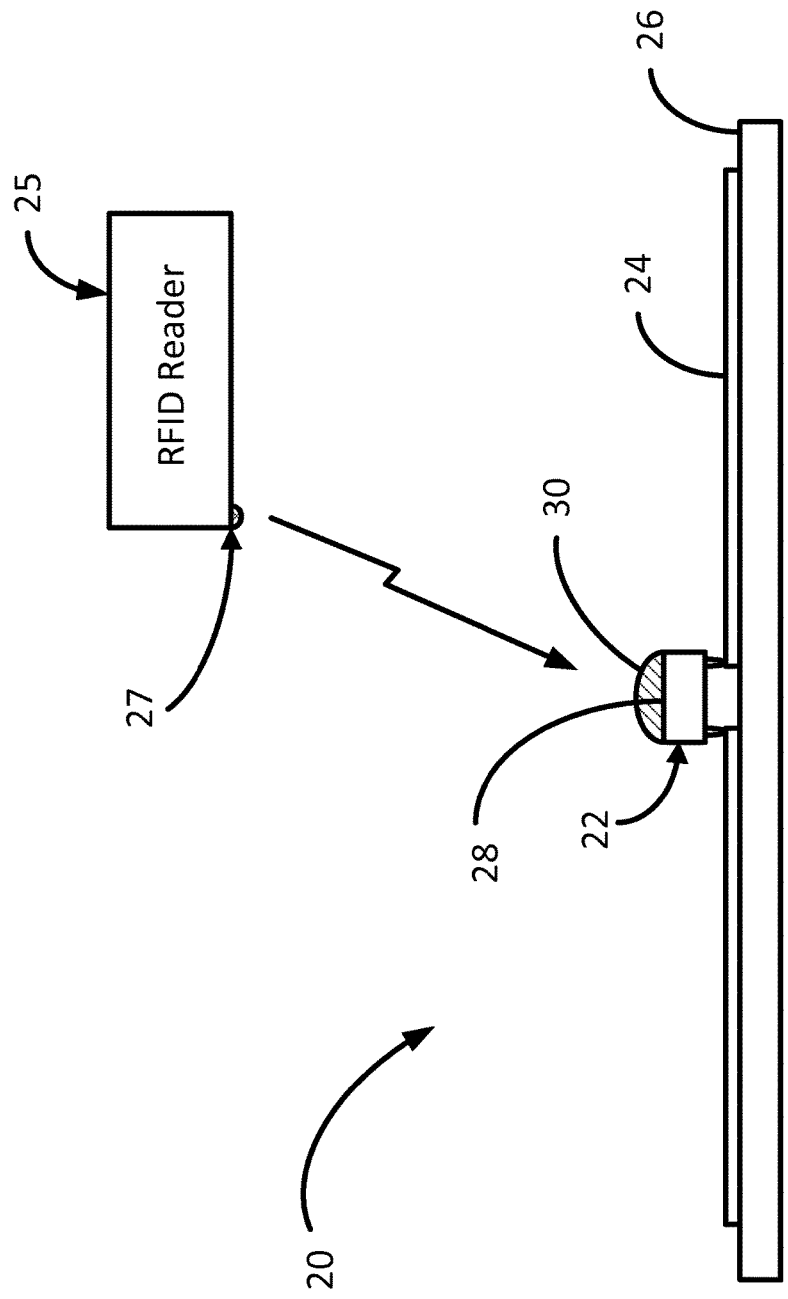
FIG. 3 is a schematic view depicting the RFID sensor of FIG. 1 and a light source in accordance with another embodiment.

The light source 27 can be configured to broadcast light generally beneath the RFID reader 25. As the RFID reader 25 is passed over different RFID sensors (e.g., 20), light can be provided to each RFID sensor that passes beneath the light source 27. In an alternative embodiment, as illustrated in FIG. 3, the light source 27 can comprise a laser guided light source that is configured to direct a concentrated beam of light towards the RFID sensor 20. In such an embodiment, the RFID reader 25 can be configured to detect the location of the RFID sensor 20 and direct the focused beam towards the sensing material 30. The RFID sensor 20 can be provided with a detectable marker, such as a visible indicia, provided on the sensing material 30. Alternatively, a ring or other structure that is retro-reflective at the wanted optical wavelength can be provided, with the optically sensitive portion of the RFID chip placed in the centre or other known location. The RFID reader 25 can locate the detectable marker during a scanning function and can direct the light beam to the detectable marker. In lieu of or in addition to the detectable marker, the RFID reader 25 can be configured to scan for and maintain focus with the sensing material 30 by using the reply signal from the RFID sensor 20 as a feedback signal.

Figure 4:
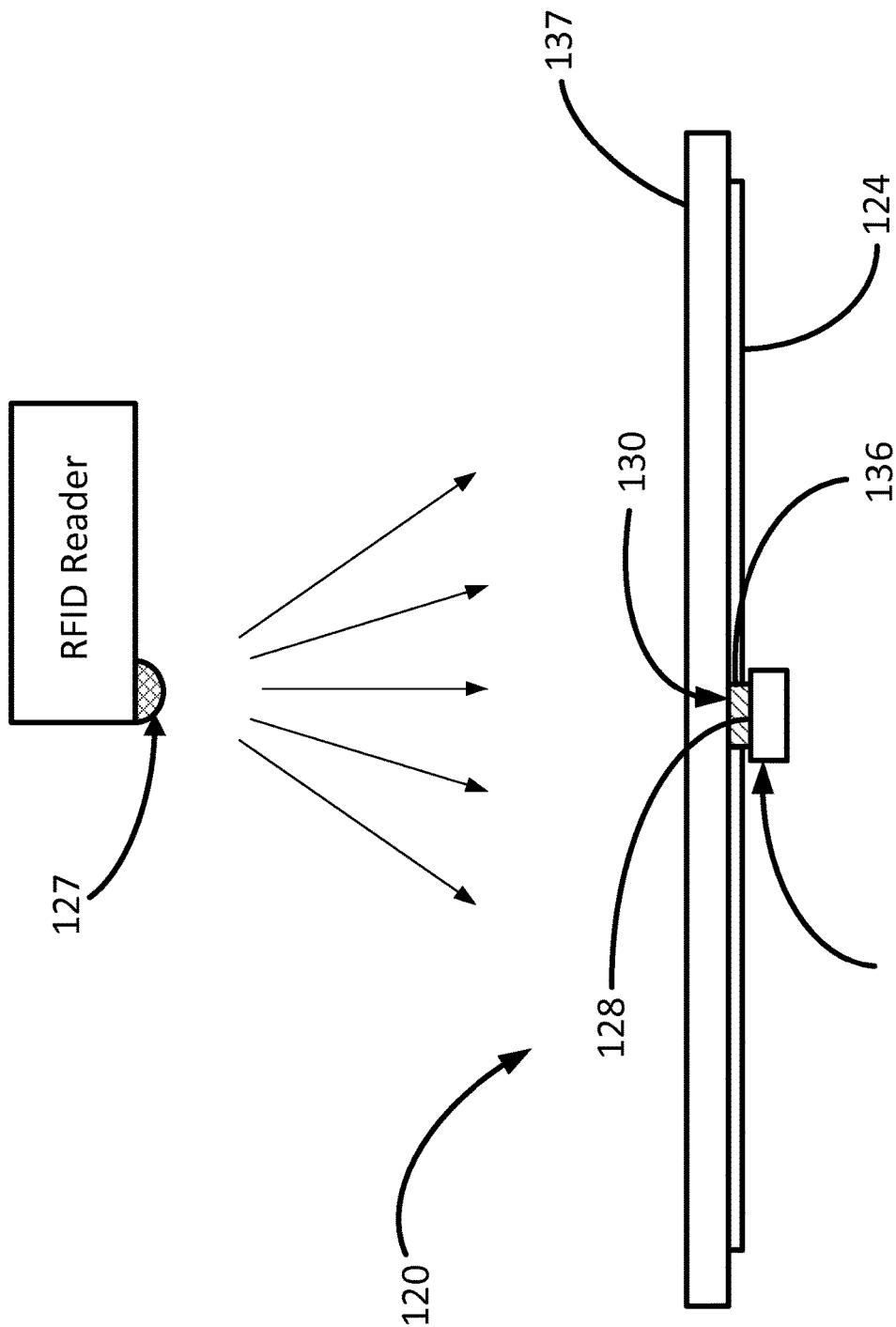
FIG. 4 is a schematic view depicting an RFID sensor and an RFID reader in accordance with yet another embodiment.

FIG. 4 illustrates an RFID sensor 120 according to another embodiment. The RFID sensor 120 shown in FIG. 4 can be similar or the same in many respects to the RFID sensor 20 shown FIG. 1. For example, the RFID sensor 120 can include an RFID chip 122 and an antenna 124 electrically coupled with the RFID chip 122. The RFID sensor 120 can include a sensing material 130 positioned proximate to an upper surface 128 so that the sensing material 130 is positioned between a source of light and the upper surface 128 of the RFID chip 122. The RFID sensor 120 can be selectively illuminated with light from a light source 127. The antenna 124, however, can overlie the RFID chip 122 and sensing material 130. The antenna 124 can be configured to define a viewing aperture 136 that permits light to reach the sensing material 130 through the antenna 130. The RFID sensor 120 can also include a substrate 137 that overlies the antenna 130 and prefilters light for the sensing material 130. The substrate 137 can be configured to filter wavelengths of light that could interfere with the sensing material 130.

Figure 5:
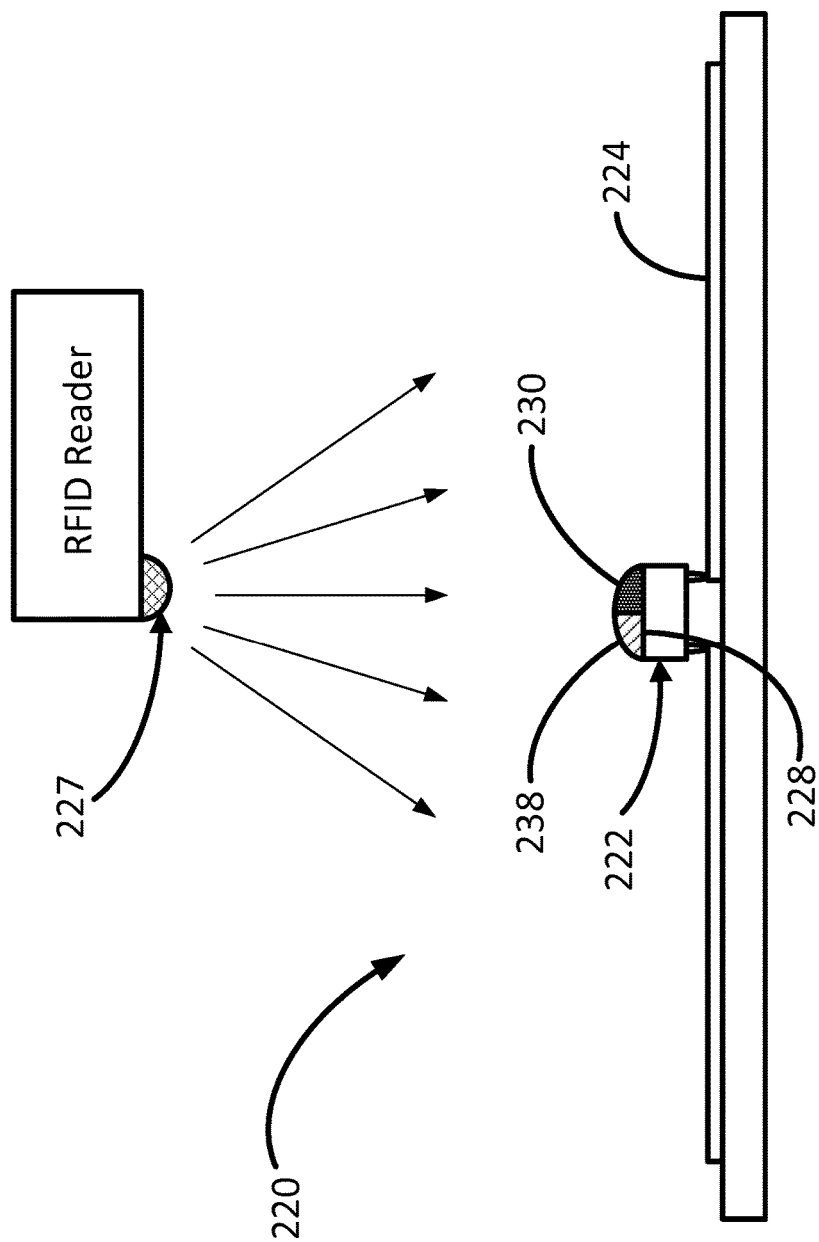
FIG. 5 is a schematic view depicting an RFID sensor and an RFID reader in accordance with still another embodiment.

FIG. 5 illustrates an RFID sensor 220 according to another embodiment. The RFID sensor 220 shown in FIG. 5 can be similar or the same in many respects to the RFID sensor 20 shown FIG. 1. For example, the RFID sensor 220 can include an RFID chip 222 and an antenna 224 electrically coupled with the RFID chip 222. The RFID sensor 220 can include a sensing material 230 positioned proximate to an upper surface 228 so that the sensing material 230 is positioned between a source of light such and the upper surface 228 of the RFID chip 222. The RFID sensor 220 can be selectively illuminated with light from a light source 227. The RFID sensor 220, however, can comprise a reference sensing material 238 positioned proximate to an upper surface 228 so that the reference sensing material 238 also is positioned between a source of light and the upper surface 228 of the RFID chip 222 and adjacent to the sensing material 230. The reference sensing material 238 can be configured to filter light uniformly (e.g., without being affected by the sensed condition or parameter). When light is projected onto the RFID sensor 220, the difference in the response of the RFID chip 222 to the light filtered through the sensing material 230 and the light filtered through the reference sensing material 238 can be compared to determine the magnitude of the sensing condition or condition or parameter.

In another embodiment, the surface of the chip may be coated with a sensing material and a reference material, where the two materials transmit a different polarization of light, either linear or circular. In operation, the illuminating source would measure the property of the RFID chip altered by illumination whilst switching between the relevant polarizations, allowing a differential measurement to be carried out.

Figure 6:
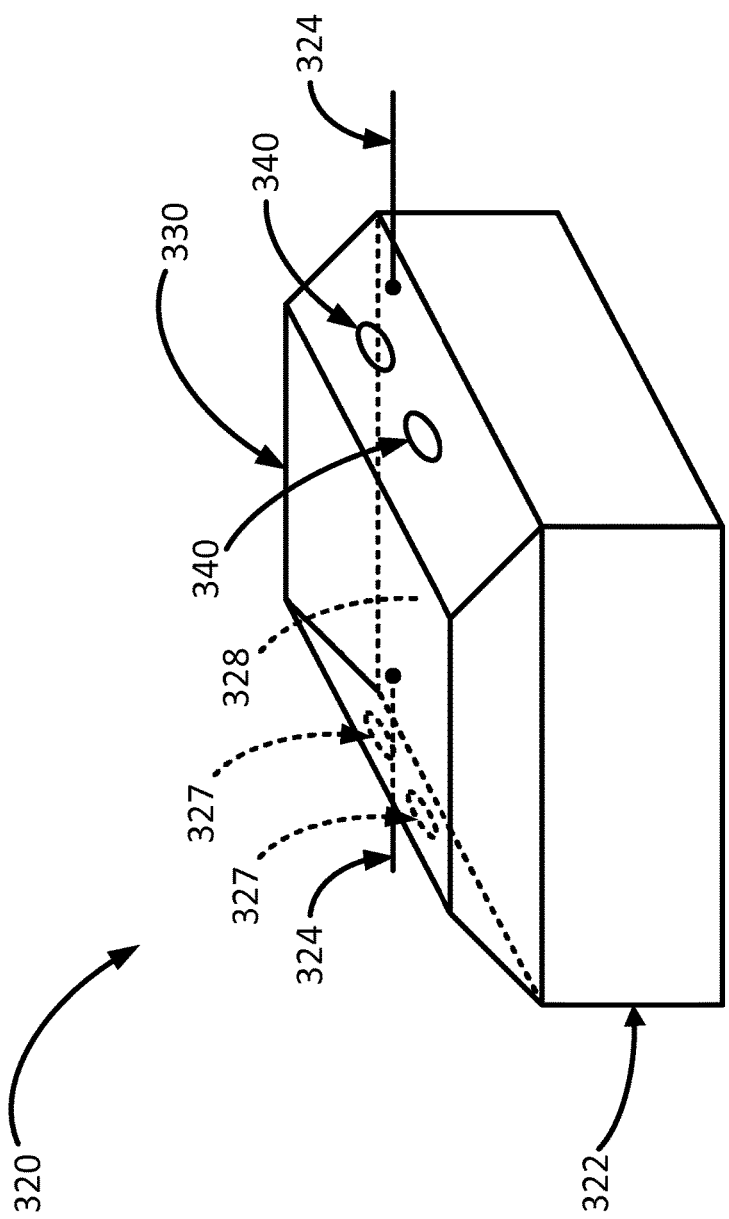
FIG. 6 is a perspective view depicting an RFID sensor according to another embodiment.

FIG. 6 illustrates a RFID sensor 320 according to another embodiment. The RFID sensor 320 shown in FIG. 6 can be a variant with on-chip illumination-type sensor and can be similar or the same in many respects to the RFID sensor 20 shown in FIG. 1. For example, the RFID sensor 320 can include an RFID chip 322 and an antenna 324 electrically coupled with the RFID chip 322. The RFID sensor 320 can include a sensing material 330 positioned between a light source and an upper surface 328 of the RFID chip 322. The RFID sensor 320, however, can comprise a pair of on-board light sources 327 that are integrated into the sensing material 230. The on-board light sources 327 can provide light to a pair of optically sensitive areas 340 defined by the RFID chip 322 and located opposite the light sources 327. When the sensing material 330 changes in response to the sensed condition or parameter, the light transmitted from the on-board light sources 327 can be filtered accordingly and detected by the optically sensitive areas 340 to facilitate detection of the sensed condition or parameter. The on-board light sources 327 can comprise a light emitting diode, an electroluminescent material, or any of a variety of integrated light emitting devices. In one embodiment, the on-board light sources 327 can be configured to transmit light at different optical frequencies and/or to utilize filters on detectors. The RFID chip 322 can be configured to perform spectrophotometry (e.g., to measure color change) or detect other changes in the sensed material 322 (e.g., material polarization and/or refractive index) to facilitate detection of the sensed condition or parameter.

In one embodiment, the on-board light sources 327 can be active-type sources such that they are powered with an on board power source, such as a battery, for example. In another embodiment, the on-board light sources 327 can be passive-type sources that are powered with a signal from a remote device, such as an RFID reader. In one example, the on-board light sources can be powered with a signal from a near field communication (NFC) reader such as might be incorporated on a smartphone. A product, such as a pregnancy test, can be provided with an RFID sensor that is configured to react to a human hormone. Once the product has been exposed to the human hormone, the RFID sensor can be moved within range of the smartphone. A signal from the NFC reader on the smartphone can be transmitted to the product to power the RFID chip 322 and the on-board light sources 327. The RFID chip 322 can respond with a reply signal to the NFC reader notifying the NFC reader of the presence and/or concentration of the human hormone.

In an alternative embodiment, the RFID sensor 320 can include a pair of electromagnetic sources (not shown) in lieu of the on-board light sources 327 and the RFID chip 322 can include a pair of electromagnetically sensitive areas in lieu of the optically sensitive areas 340. The electromagnetic sources can be configured to emit electromagnetic energy in the direction of the electromagnetically sensitive areas. The sensing material 330 can be configured to vary the electromagnetic energy from the electromagnetic sources in response to the sensed condition or parameter.

Figure 7:
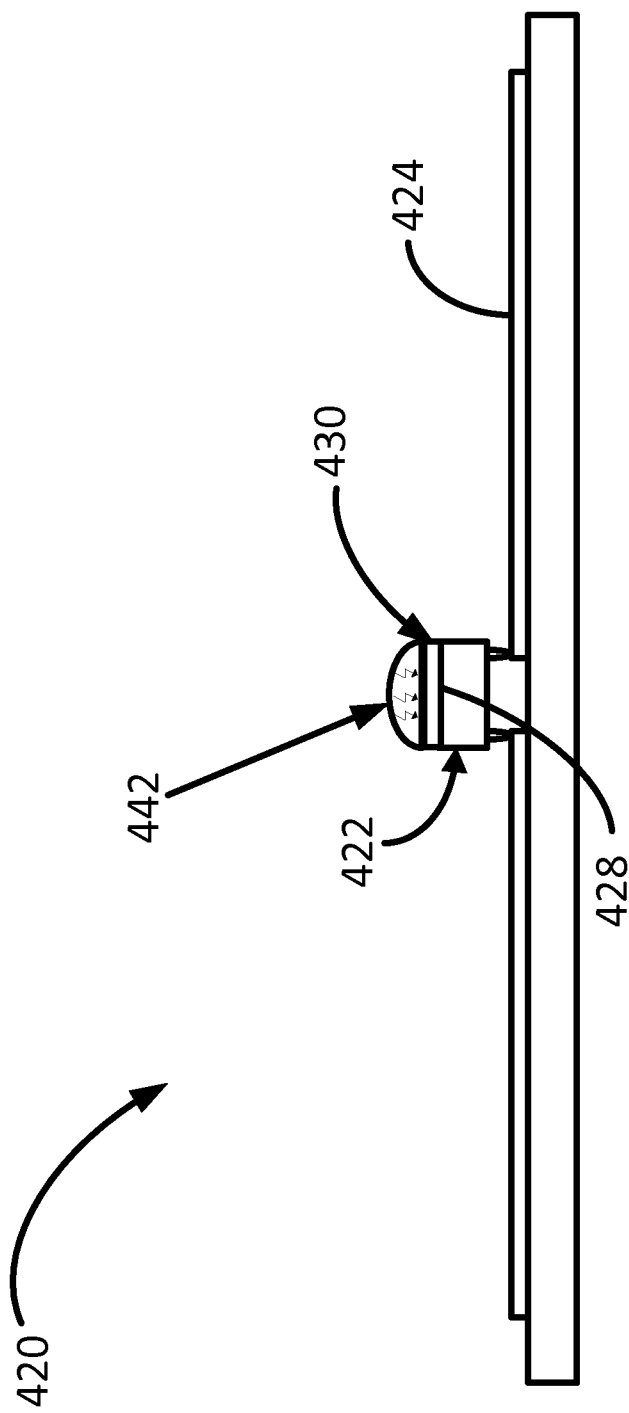
FIG. 7 is a schematic view depicting an RFID sensor and an RFID reader in accordance with still another embodiment.

FIG. 7 illustrates an RFID sensor 420 according to another embodiment. The RFID sensor 420 shown in FIG. 7 can be similar or the same in many respects to the RFID sensor 20 shown FIG. 1. For example, the RFID sensor 420 can include an RFID chip 422 and an antenna 424 electrically coupled with the RFID chip 422. The RFID sensor 420 can include a sensing material 430 positioned proximate to an upper surface 428 so that the sensing material 430 is positioned between a source of light and the upper surface 428 of the RFID chip 422. An illuminating material 442 can be positioned on the sensing material 430. The illuminating material 442 can comprise a chemoluminescent material that produces light in response to the sensed condition or parameter. The amount of light produced by the illuminating material 442 can depend upon the presence and/or concentration of the sensed condition or parameter. The RFID chip 422 can detect the light from the illuminating material 442 to facilitate detection of the sensed condition or parameter. In one example, where the sensed condition or parameter is a reducing agent, the presence of the reducing agent could trigger the illuminating material to emit light that is then detected by the RFID chip 422 to facilitate detection of the reducing agent. In another embodiment, the illuminating material can be positioned directly proximate to the surface of the RFID chip without a sensing material being placed in between. The illuminating material can be arranged so the an environmental condition or parameter can affect the amount of light generated by the illuminating material. The behavior of the RFID chip can change proportionally to or in some determinable manner with respect to the amount or light generated by the illuminating material. Therefore, the environmental condition or parameter can be ascertained from the behavior of the RFID chip upon the generating of light by the illuminating material.

In another embodiment, an RFID chip can be arranged so that it includes a plurality of photosensitive areas, each with a different sensing material positioned between the photosensitive area and the light source. Such an arrangement the spectrum of the light transmitted through the various sensing material can be determined.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art.

What is claimed is:

1. A method for detecting properties or conditions of an environment comprising:
   overlaying a sensing material onto a surface of a first RFID chip having a structure to form a RFID sensor, configuring the first RFID chip to function as an optical sensor;

introducing a second RFID chip that has an inert material and the second RFID chip is part of the structure of the first chip;

configuring the sensing material to function as a variable light filter that filters light differently depending upon the properties or conditions of the environment surrounding the RFID sensor;

directing light from a light source towards the RFID sensor and the second chip and the light source is selectively operated by an RFID reader wherein the RFID reader periodically activates the light source to monitor the change in a condition or parameter over time and an amount of light permitted through to the sensing material is a function of a presence or concentration of the sensed condition or parameter; and detecting the response of the RFID sensor and looking at the difference between a response from each of the first and second chip in response to the light.

2. The method of claim 1, wherein the second RFID chip has the same sensing material isolated from the environment.

3. The method of claim 1, wherein the light source can remain on during the operation of the RFID reader.

4. The method of claim 1, further comprising determining the magnitude of the presence or concentration of the sensed condition or parameter based at least in part on a comparison of the difference between a response from each of the first RFID chip and the second RFID chip.

5. The method of claim 1, where the condition or parameter is at least one of the group including humidity, temperature, atmospheric pressure, and pH.

6. The method of claim 1, where the properties or conditions of the environment surrounding the RFID sensor alter or modify the sensing material.

7. The method of claim 1, where the configuring step comprises configuring the sensing material to function as a variable near-infrared light filter that changes at least one of its color or opacity in response to the sensed condition or parameter.

8. The method of claim 1, where the light source is selectively operated by the RFID reader based upon the communication status between the RFID reader and the RFID sensor.

9. The method of claim 1, where an opacity of the sensing material varies in response to a change in the presence or concentration of the sensed condition or parameter.

10. The method of claim 9, where the higher the presence or concentration of the sensed condition or parameter, the less light is allowed to pass through the sensing material.

11. The method of claim 1, where a reflectivity of the sensing material varies in response to a change in the presence or concentration of the sensed condition or parameter.

12. The method of claim 1, where an absorption of the sensing material varies in response to a change in the presence or concentration of the sensed condition or parameter.

13. The method of claim 1, where a refractivity of the sensing material varies in response to a change in the presence or concentration of the sensed condition or parameter.

14. The method of claim 1, where a color of the sensing material varies in response to a change in the presence or concentration of the sensed condition or parameter.

15. The method of claim 14, where the sensing material comprises a thermochromic material that changes color in response to heat.

16. The method of claim 14, where the sensing material comprises a biomimetic sensor that darkens in the presence of carbon monoxide.

17. The method of claim 14, where the sensing material comprises one of a titanium oxide compound or a palladium oxide compound that changes color in the presence of hydrogen gas.

18. The method of claim 1, further comprising attaching the RFID sensor to a shipping container to monitor for levels of relative humidity.

19. The method of claim 1, where the condition or parameter comprises one or more bio-hazardous materials.

20. The method of claim 19, further comprising providing the RFID sensor as part of a public transportation system to monitor for levels of the one or more bio-hazardous materials.

* * * * *